United States Patent [19]
Grycewicz

[11] Patent Number: 5,428,452
[45] Date of Patent: Jun. 27, 1995

[54] OPTICAL FOURIER TRANSFORM METHOD FOR DETECTING IRREGULARITIES UPON TWO-DIMENSIONAL SHEET MATERIAL SUCH AS FILM OR TAPE

[75] Inventor: Thomas J. Grycewicz, Belmont, Mass.

[73] Assignee: The United States of America as represented by the Secretary of the Air Force, Washington, D.C.

[21] Appl. No.: 192,470

[22] Filed: Jan. 31, 1994

[51] Int. Cl.⁶ ............................................. G01N 21/89
[52] U.S. Cl. ............................................. 356/430
[58] Field of Search ................................ 356/237, 430

[56] References Cited

U.S. PATENT DOCUMENTS

| | | | |
|---|---|---|---|
| 3,614,232 | 10/1971 | Mathisen | 356/237 X |
| 3,658,420 | 4/1972 | Axelrod | 356/237 X |
| 3,879,131 | 4/1975 | Cuthbert et al. | 356/237 X |
| 4,501,492 | 2/1985 | Douklias | 356/73.1 |
| 5,185,638 | 2/1993 | Conzola et al. | 356/237 |
| 5,218,417 | 6/1993 | Gay et al. | 356/300 |
| 5,225,886 | 7/1993 | Koizumi et al. | 356/237 |
| 5,225,890 | 7/1993 | Lee et al. | 356/371 |
| 5,264,912 | 11/1993 | Vaught et al. | 356/237 |

FOREIGN PATENT DOCUMENTS 2126716 3/1984 United Kingdom ................ 356/237

*Primary Examiner*—Vincent P. McGraw
*Attorney, Agent, or Firm*—Robert L. Nathans; Stanton E. Collier

[57] ABSTRACT

The rapidly moving uniform surface being inspected is illuminated with either laser or wide-band light. The Fourier transform of the surface is produced upon the detector plane of an electronic camera. In the absence of defects, the transform light energy is produced only in the center of the detector plane but in the presence of defects light is produced in various non-centralized portions of the detector plane which can indicate the orientation and size of the defect.

5 Claims, 1 Drawing Sheet

OPTICAL FOURIER TRANSFORM METHOD FOR DETECTING IRREGULARITIES UPON TWO-DIMENSIONAL SHEET MATERIAL SUCH AS FILM OR TAPE

STATEMENT OF GOVERNMENT INTEREST

The invention described herein may be manufactured and used by or for the Government for governmental purposes without the payment of any royalty thereon.

BACKGROUND OF THE INVENTION

The present invention relates to the field of defect inspection devices.

Current automated inspection systems work by having an electronic image sensor or camera take a series of snapshots of the area to be inspected. These snapshots are then processed digitally. The processing typically looks for pixels in the image which deviate significantly from the normal brightness level. Once such a pixel is found, the computer records its location. When enough deviations are found closely grouped together, a defect is declared.

A limitation of current systems is that they process data as a series of still images. These can be captured by strobe photography as the inspected surface moves by the image sensor or they can be photographed when the inspected surface is still. Overlapping images of the surface to be inspected are digitized and processed by a computer. For 100 percent inspection, the overlap must be large enough so that a defect cannot hide in the "crack" between images. Often there is no overlap, or there might even be a space between frames. The result is less than 100 percent inspection of the surface. In order to inspect a large surface in a short time, very high data transfer rates and processing rates are required. For example, if a 0.001 inch wide scratch is unacceptable on a 0.5 inch wide magnetic tape, which is to be inspected at at a rate of five feet per second, a data transfer and processing rate of thirty million pixels per second would be required. Thus, even a modest inspection task can be very burdensome to the computer involved in the inspection process.

BRIEF SUMMARY OF THE INVENTION

In accordance with the invention, a method of very quickly inspecting a uniform surface for scratches or other small defects is provided. This includes, but is not limited to, the inspection of thin films placed on flexible media such as magnetic tape and photographic film. A lens placed one focal length from the surface obtains the spatial Fourier transform of the illuminated area to be inspected. If the input image is uniform, the energy in the Fourier plane is concentrated in a small spot at the center of the Fourier light pattern image. If defects are present, light in the non-centralized image regions is produced and detected by an image sensor at the Fourier plane. Also, the orientation of the defects can be detected and recorded. Any light source can be used to illuminate the surface. Laser light is not required as wideband illumination produces satisfactory results for this application of the Fourier transform used to detect elongated defects such as scratches.

Relative motion between the lens and the media under inspection does not adversely affect this inspection process. The inspection process can operate at very high speeds since there is no need to freeze the image in order to process the data. The amount of information which which must be processed electrically is reduced from a data stream which could overwhelm a supercomputer, to a modest amount of data easily processed by a PC.

BRIEF DESCRIPTION OF THE DRAWINGS

Other features of the invention will become apparent upon study of the following description taken in conjunction with the drawings in which:

FIGS. 2 and 3 schematically illustrate the results of the inspection of a defect free surface under test, while

DETAILED DESCRIPTION OF EMBODIMENTS OF THE INVENTION

Figure 1:
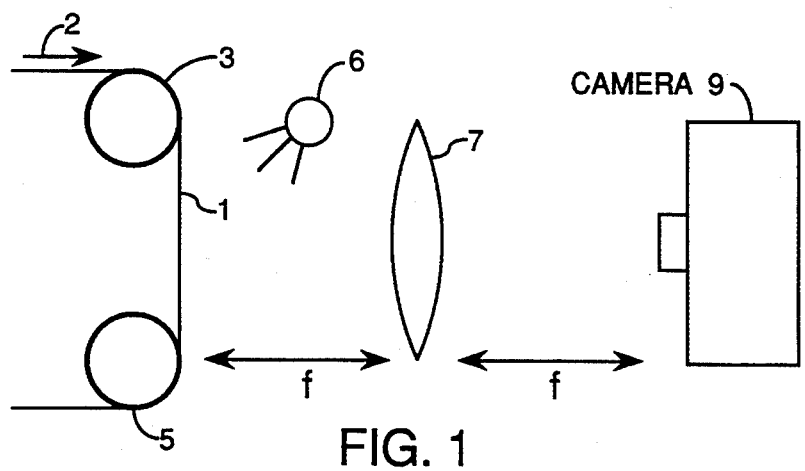
FIG. 1 discloses a preferred embodiment of the invention.

In FIG. 1, a sheet 1 is driven over rollers 3 and 5 continuously as indicated by arrow 2. The sheet can be photographic film, magnetic tape or the like, to be inspected for defects such as scratches. Light source 6 illuminates the sheet with either monochromatic light or wideband light so that with such wide-band illumination, a laser need not be employed. A lens 7 is positioned between the surface being inspected and an electronic camera or image sensor 9. The lens is separated from the image sensor and the sheet by a distance of one focal length of the lens. Thus the lens obtains the Fourier transform of the surface under inspection which is manifested as a light pattern which is detected by the image sensor 9.

Figure 5:
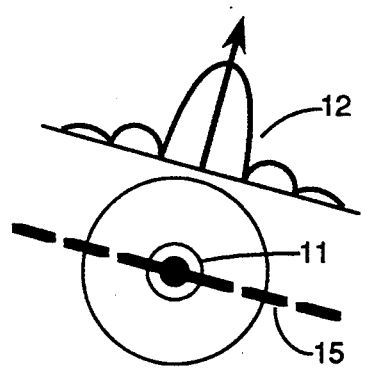

Images which have slow spatial variations in energy will result in some of the Fourier plane energy being directed a small distance from the centralized region 11, while fast intensity variations of input images result in a significant amount of energy being produced at a substantial distance away from the centralized region as shown in FIG. 5. If the surface being inspected is supposed to be uniform, any significant energy substantially displaced from the centralized portion indicates the presence of a defect.

Figure 2:
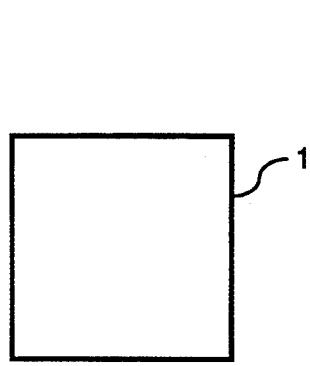
Figure 3:
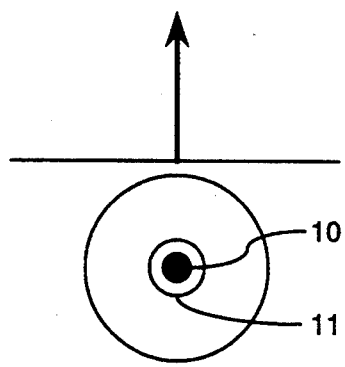
Figure 4:
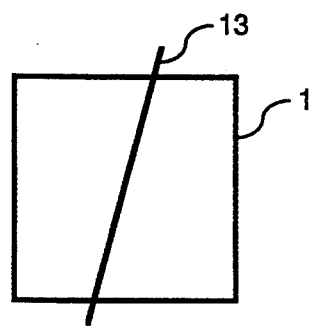
FIGS. 4 and 5 illustrate the results of the detection of an elongated scratch.

If the surface inspected is free of defects, the image produced in the Fourier plane will form a predictable pattern. Deviations from the pattern are indicative of defects. The case of a uniform surface is shown in FIGS. 2 and 3. If a uniform surface is free of defects, the transform will consist of a spot of light 10 positioned only in a centralized portion 11 in the image plane of the image sensor. However, if the defect consists of an elongated scratch 13, the Fourier transform is manifested as an elongated light pattern 15, which is readily detected by the image sensor. For monochromatic illumination of the sheet 1, the scratch 13 produces a transform whose intensity is a sinc function 12 as shown in FIG. 5. Monochromatic illumination is not required. Using wideband illumination instead, simply destroys the observed periodicity of the sinc function sidelobes, and the result is a radial pattern which is still a very detectable signal.

It may be advantageous to design a specialized detector for the Fourier plane. When very high data processing speeds and/or system simplicity are desired, the large number of pixels in a conventional CCD camera may be limiting. For the detection of defects in a smooth uniform surface, a detector having a small number of relatively large pixels is adequate. For example, the detector plane could have only five discreet detectors for the five sectors shown in FIG. 6. These detectors should be arranged such that the majority of the signal in the Fourier plane falls on a single detection region or a small number of detection regions. This allows defects to be detected with a higher signal to noise ratio in the detection process.

Figure 6:
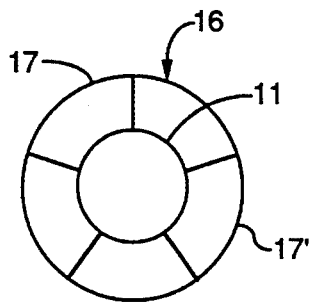
FIG. 6 illustrates the partitioning of a detection region which will optimize detection of illumination in the Fourier plane due to an elongated defect such as a scratch.

If the goal is the detection of scratches, an annular detection region 16 segmented into wedge shaped subregions 17 and 17' is provided as shown in FIG. 6. The advantage of using an odd number of detection sectors such as five is that if the detected radial pattern 15 from a scratch is split between detection areas on one side of the detector plane, it is centered on the other side. If the expected direction of scratches in a surface is known, this can be used to optimize the size and placement of the wedge shaped detection regions. Since the detected Fourier pattern of a scratch falls along a radial line, this will result in the detected energy being focused on small portions of the total annular detection region 16. Radial segmentation of the detection region enhances the signal-to-noise ratio. For example, the light pattern 15 in FIG. 5 would be detected within opposite CCD target portions 17 and 17' in FIG. 6. Note that the transform portions 15 are oriented perpendicular to the scratch 13. The electronics co-acting with the image sensor to determine the orientation of the elongated transform portions 15 is well within the skill of the workers in the art and need not be described herein in the interests of brevity and economy. Since such orientation of the light pattern of the transform can be easily sensed by the image sensor, the orientation of the defect 13 perpendicular thereto can be recorded.

If the surface to be inspected contains a regular spatially periodic pattern such as a wire mesh screen, it can still be inspected in accordance with the invention. Using monochromatic or quasi-chromatic light for illumination, a regular Fourier transform light pattern is expected in the Fourier plane. A significant deviation or change from this pattern indicates the presence of a defect.

Figure 7:
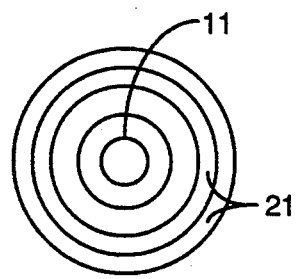
FIG. 7 illustrates the partitioning of the detection region to optimize detection of the presence of a roughly circular defect.

Alternatively, if the goal is to detect defects which which appear as small blobs with approximately with the same diameter in all directions, the detection region can be partitioned into annular rings 21 surrounding centralized region 11 as shown in FIG. 7. In this manner, a limited amount of information regarding the size of the defect may be obtained. To obtain defect size information in this way requires using monochromatic or quasi-monochromatic illumination.

The well known process of taking the Fourier transform optically is normally considered to be a monochromatic or quasi-monochromatic process. This is important if the system is used to obtain detailed information about the spatial variation content of the input image. In the case of defect detection, the object is to detect any spatial variation over a range of spatial frequencies. Thus as mentioned above, incoherent radiation over a broad band of frequencies will suffice for the inspection of uniform surfaces such as film or tape.

The intensity of the transform of any feature on the surface of the sheet 1 is independent of the location of this defect in the image plane. The transform of the defect will thus be detected at a static location as long as the defect is anywhere in the image plane. If the input image is moving, the limit on detectability of a signal is that the defect be in the image plane long enough so that a detectable amount of energy can be integrated in the detection region. This limit is far easier to meet than the limits imposed by the previously mentioned data transfer of bit mapped image information in a high speed inspection process.

If the inspection area has a sharp edge, this will be interpreted as a large feature with high spatial frequency content in a direction perpendicular to the edge. One solution to this problem is to taper the edges of the illumination on the inspected surface. This taper should be slow when compared to the spatial frequencies present in the defects to be detected. In addition, a filter may be placed between the lens and the surface being inspected to cause the energy received from the edges of the inspection area to taper off slowly and smoothly.

If the surface contains sharp straight line or edge features in a few known directions, the detection plane can be masked so that sharp features in specific directions are not detected. However, defects whose fast variations are perpendicular to these features, such as a scratch parallel to a feature edge cannot be detected.

In the Fourier plane, the transform intensity of the higher orders of a dark feature on a light background is identical to that of a light feature on a dark background. Since the detector is sensitive to the rate of intensity change, a light on dark defect is just as easy to detect as a dark on light defect.

The detected signal is integrated over the detection period of the camera. In contrast with taking snapshots, the camera may continuously view the surface under inspection moving thereunder. Thus a large surface area may be inspected during the defect detection period. The fundamental limitation to the length of time over which one integrates is determined by the signal to noise ratio of the detector system. Generally the goal will be to detect one or a few defects which results in large quick spikes in the output. The noise will be present at a constant low level, and the noise output will ramp up as the signal is integrated. At some point this noise output will become large enough that a defect response can no longer be reliably detected.

Other embodiments of the invention will become apparent to the workers in the art, and thus the scope of the invention is to be limited only by the terms of the following claims and art recognized equivalents.

What is claimed is:

1. Apparatus for detecting defects in two-dimensional sheet material which may have defects therein comprising:
    (a) illumination means for illuminating said two-dimensional sheet material which may have defects therein;
    (b) a stationary lens means having an optical axis intersecting said two-dimensional sheet material for producing a Fourier transform of the surface of said two-dimensional sheet material which may have defects therein;
    (b) drive means for driving said two-dimensional sheet material past said stationary lens; and
    (c) a light sensor means, positioned in the Fourier transform plane of said stationary lens, and having an off-axis non-centrally positioned light detector means for detecting light energy produced when a sheet material defect passes by said stationary lens means.

2. The apparatus of claim 1 wherein said light sensor means includes an on-axis centrally positioned light detector.

3. The apparatus of claim 1 wherein said off-axis non-centrally positioned light detector means comprises an odd number of discreet detector sectors surrounding the optical axis.

4. The apparatus of claim 2 wherein said off-axis non-centrally positioned light detector means comprises an odd number of detector sectors surrounding the optical axis.

5. The apparatus of claim 1 wherein said drive means drives said two-dimensional sheet material continuously past the stationary lens means at high speeds, thereby to expedite rapid inspection of large quantities of said two-dimensional sheet material.

* * * * *